United States Patent [19]

Wadham et al.

[11] Patent Number: 4,767,406
[45] Date of Patent: Aug. 30, 1988

[54] SYRINGE PUMPS

[75] Inventors: Paul Wadham, Winchester; Walter H. Cox, Weybridge; Ching B. Lim, Basingstoke, all of Great Britain

[73] Assignee: Vickers Plc., London, Great Britain

[21] Appl. No.: 917,712

[22] Filed: Oct. 10, 1986

[30] Foreign Application Priority Data

Oct. 11, 1985 [GB] United Kingdom ............... 8525109

[51] Int. Cl.$^4$ .......................................... A61M 37/00
[52] U.S. Cl. ..................................... 604/155; 604/67
[58] Field of Search ................ 604/155, 154, DIG. 1, 604/DIG. 12, 67; 128/65

[56] References Cited

U.S. PATENT DOCUMENTS

| 3,631,847 | 1/1972 | Hobbs, II | 604/155 |
| 3,858,581 | 1/1975 | Kamen | 604/155 |
| 4,405,318 | 9/1983 | Whitney et al. | 604/155 |
| 4,424,720 | 1/1984 | Bucchianeri | 604/155 |
| 4,435,173 | 3/1984 | Siposs et al. | 604/155 |
| 4,617,016 | 10/1986 | Blomberg | 604/155 |

Primary Examiner—John D. Yasko
Attorney, Agent, or Firm—Pearne, Gordon, McCoy & Granger

[57] ABSTRACT

A syringe pump comprises (a) a casing; (b) within said casing, a motor (c) an externally screw-threaded drive rod connected at one end thereof to said motor so that, in use, the motor can rotate the drive rod about its axis, the other end of said drive rod being free to rotate in a journal bearing; (d) a carriage mounted for sliding movement within said casing and driveably mounted on said drive rod in engagement with the external screw-thread thereof; (e) a strain gauge operatively connected to measure the torque reaction between said motor and said carriage when the carriage acts, in use, against the plunger of a syringe to expel fluid from the syringe; (f) means located externally of the main body of the casing for holding a syringe in position on the syringe pump; (g) means for sensing the position of said carriage with respect to the ends of said drive rod; (h) a microprocessor arranged to receive input signals from said strain gauge and said carriage position sensing means and to derive therefrom (when the syringe pump is in use) firstly the fluid delivery rate and secondly the fluid delivery pressure; and (i) a control system, acting through said microprocessor, to input operating commands to the syringe pump.

14 Claims, 6 Drawing Sheets

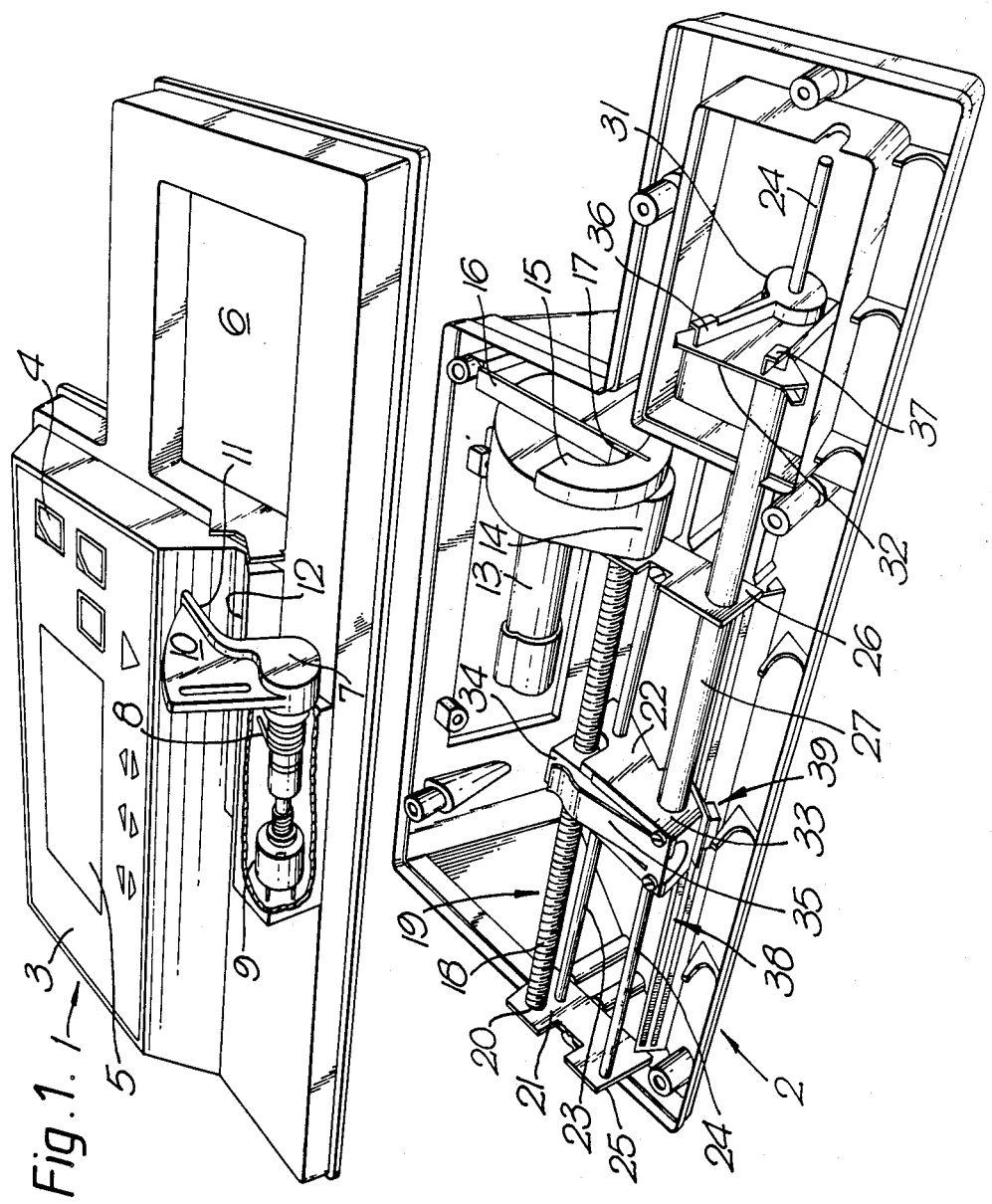

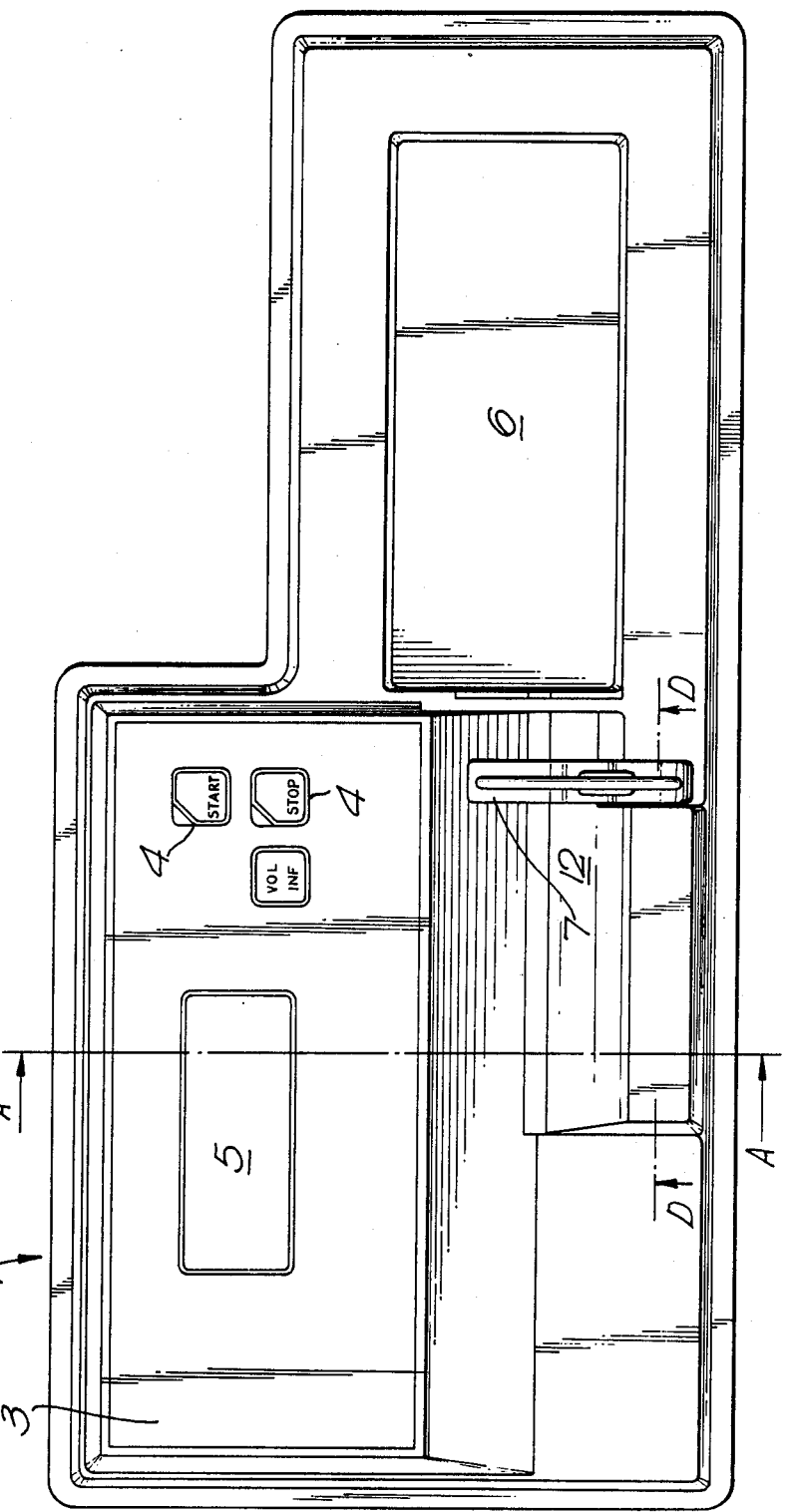

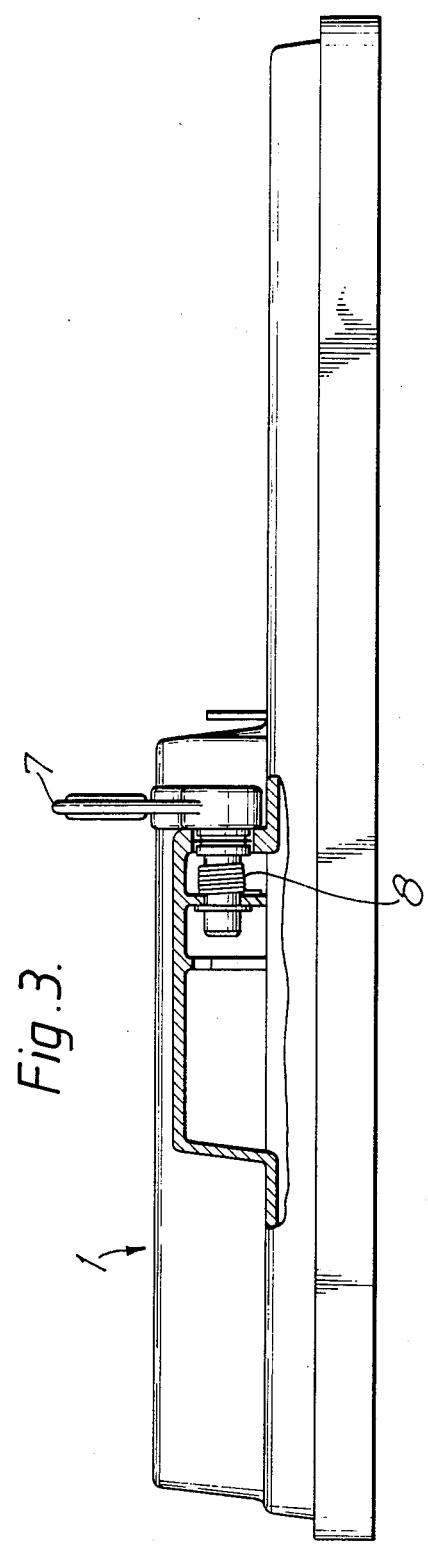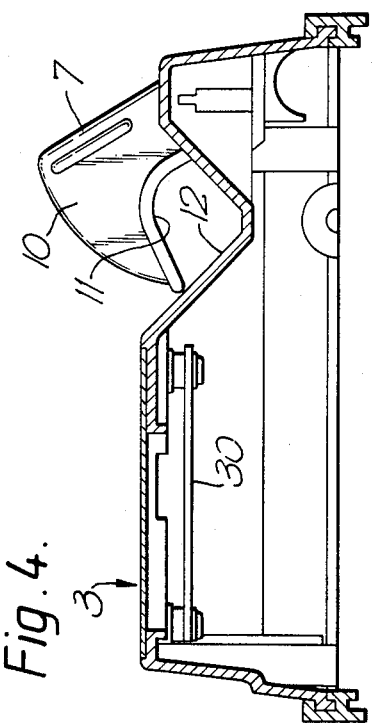

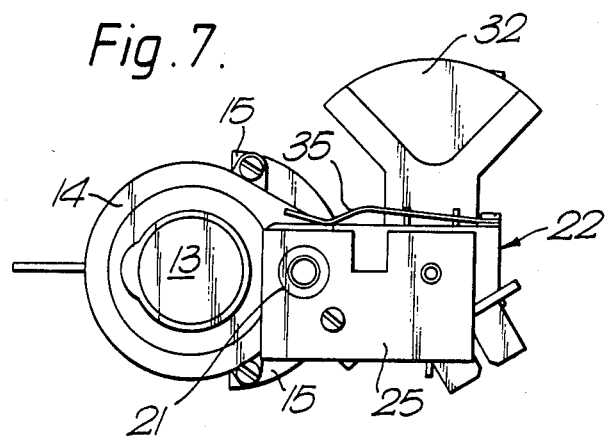
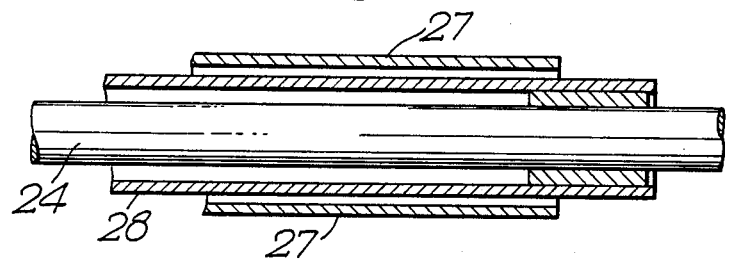
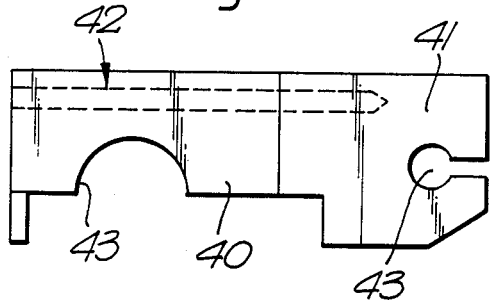

SYRINGE PUMPS

BACKGROUND OF THE INVENTION

This invention relates to syringe pumps i.e. drive units for effecting precise operation of a syringe.

Syringe pumps are used widely in health care and in particular where it is necessary to control accurately the delivery of a fluid to a patient. This is particularly important in low-dosage critical drug therapy, e.g. as occurs in coronary and neo-natal care. In such fields, there is a constant need to increase the reliability, safety and accuracy of syringe pumps. Two areas of particular importance are the determination of fluid delivery pressure, so as to prevent operation of the syringe pump at pressures which would be damaging to the patient; and accurate metering of the quantity of fluid delivered to the patient. Embodiments of the present invention aim to provide improvements in these two areas.

SUMMARY OF THE INVENTION

According to one aspect of the present invention, there is provided a syringe pump which comprises:

(a) a casing;
(b) within said casing, a motor;
(c) an externally screw-threaded drive rod connected at one end thereof to said motor so that, in use, the motor can rotate the drive rod about its axis, the other end of said drive rod being free to rotate in a journal bearing;
(d) a carriage mounted for sliding movement within said casing and driveably mounted on said drive rod in engagement with the external screw-thread thereof;
(e) a strain gauge operatively connected to measure the torque reaction between said motor and said carriage when the carriage acts, in use, against the plunger of a syringe to expel fluid from the syringe;
(f) means located externally of the main body of the casing for holding a syringe in position on the syringe pump;
(g) means for sensing the position of said carriage with respect to the ends of said drive rod;
(h) a microprocessor arranged to receive input signals from said strain gauge and said carriage position sensing means and to derive therefrom (when the syringe pump is in use) firstly the fluid delivery rate and secondly the fluid delivery pressure; and
(i) a control system, acting through said microprocessor, to input operating commands to the syringe pump.

DESCRIPTION OF THE PREFERRED EMBODIMENTS

Preferably, the syringe pump further includes (j) a display system driven by said microprocessor to display a predetermined set of parameters relating to the operating condition of the syringe pump.

The carriage is preferably supported within the casing on one or more fixed rods. The carriage can conveniently be in two parts, one of which parts is supported by said rod(s) in a fixed orientation, and the other of which is movable to a limited extent with respect to the first part. Preferably, said second carriage part is able to pivot against the action of a biasing means away from engagement with said drive rod. A declutch arrangement is preferably provided to control the engagement and disengagement of said second carriage part from the drive rod.

The means for sensing the position of the carriage preferably comprises a reader unit attached to the carriage and positioned so as to read a position code carried, for example, by a bar coded member. Preferably, the bar coded member is a two-channel linear encoder located in the syringe pump casing at a level just beneath said carriage.

Advantageously, the means for supporting a syringe is in the form of rotary clamp means located externally of the main body of the casing and incorporating or co-operating with a position sensing device which in use generates a signal indicative of the position of the rotary clamp means about the body of a syringe. A suitable device for this purpose is a rotary potentiometer.

Preferably, the casing of the syringe pump is in two parts, an upper part and a lower part; the motor and associated drive parts can be housed in the lower casing unit, while the microprocessor and display/control elements can be located in the upper casing unit.

In a preferred embodiment of the present invention, the syringe pump comprises:

(a) a casing;
(b) within said casing, a motor;
(c) an externally screw-threaded drive rod connected at one end thereof to said motor so that, in use, the motor can rotate the drive rod about its axis, the other end of said drive rod being free to rotate in a journal bearing;
(d) a first support rail extending parallel to said drive rod;
(e) a second support rail extending parallel to said drive rod and to said first support rail;
(f) a carriage mounted for sliding movement on said first and second support rails and driveably mounted on said drive rod in engagement with the external screw-thread thereof;
(g) a strain gauge operatively connected to measure the torque reaction between said motor and said carriage when the carriage acts, in use, against the plunger of a syringe to expel fluid from the syringe;
(h) rotary clamp means located externally of the main body of the casing and incorporating an analog position sensing device capable in use of generating an output signal indicative of the position of the rotary clamp means about the body of a syringe;
(i) extending parallel to said drive rod and cooperating with said carriage, a two-channel linear encoder;
(j) a reader unit attached to said carriage and arranged to read the channels of said linear encoder;
(k) a microprocessor arranged to receive input signals from said strain gauge, said rotary clamp means and said reader unit and programmed to derive therefrom (when the syringe pump is in use) firstly the fluid delivery rate and secondly the fluid delivery pressure;
(l) a control system, acting through said microprocessor, to input operating commands to the syringe pump; and
(m) a display system driven by said microprocessor to display a predetermined set of parameters relating to the operating condition of the syringe pump.

Preferably, the rotary clamp means includes, as the position sensing device, a rotary potentiometer.

The relative disposition of the drive rod and the two support rails for the carriage is preferably such that one support rail is located beneath the drive rod, while the other support rail is laterally spaced from the drive rod and first support rail.

The output from the reader unit working in conjunction with the two-channel linear encoder enables the microprocessor to determine the absolute position of the syringe at any given time; this positional information together with the output from the analog position sensing device (e.g. rotary potentiometer) in said rotary clamp means enables the microprocessor to derive a plurality of useful parameters, including the amount of fluid delivered from a syringe. Also, the output from the reader unit working in conjunction with the two-channel linear encoder and the output from the strain gauge enable the microprocessor to calculate the fluid delivery pressure at any time.

The control and display systems operate with the microprocessor in a preselected manner to control the motor and to give displays of parameters associated with pump operation. The microprocessor will also generally be programmed to generate one or more alarm indications in the event that one or more predetermined safety parameters are violated.

BRIEF DESCRIPTION OF THE DRAWINGS

For a better understanding of the invention, and to show how the same may be carried into effect, reference will now be made by way of example, to the accompanying drawings, in which:

FIG. 1 which shows a schematic exploded view of a syringe pump, comprising an upper case assembly and a lower case assembly, in accordance with this invention;

FIG. 2 is a plan view of the upper case assembly of the pump;

FIG. 3 is a side elevational view of the assembly shown in FIG. 2;

FIG. 4 is a cross-sectional view of the lines A—A of FIG. 2;

FIG. 7 is an end elevational view of the elements shown in FIG. 5, and seen from the left;

FIG. 8 is an enlarged sectional view along the lines X—X of FIG. 5; and

FIG. 9 is a schematic sectional view of one component of the syringe pump.

DETAILED DESCRIPTION OF A PREFERRED EMBODIMENT

Figure 5:
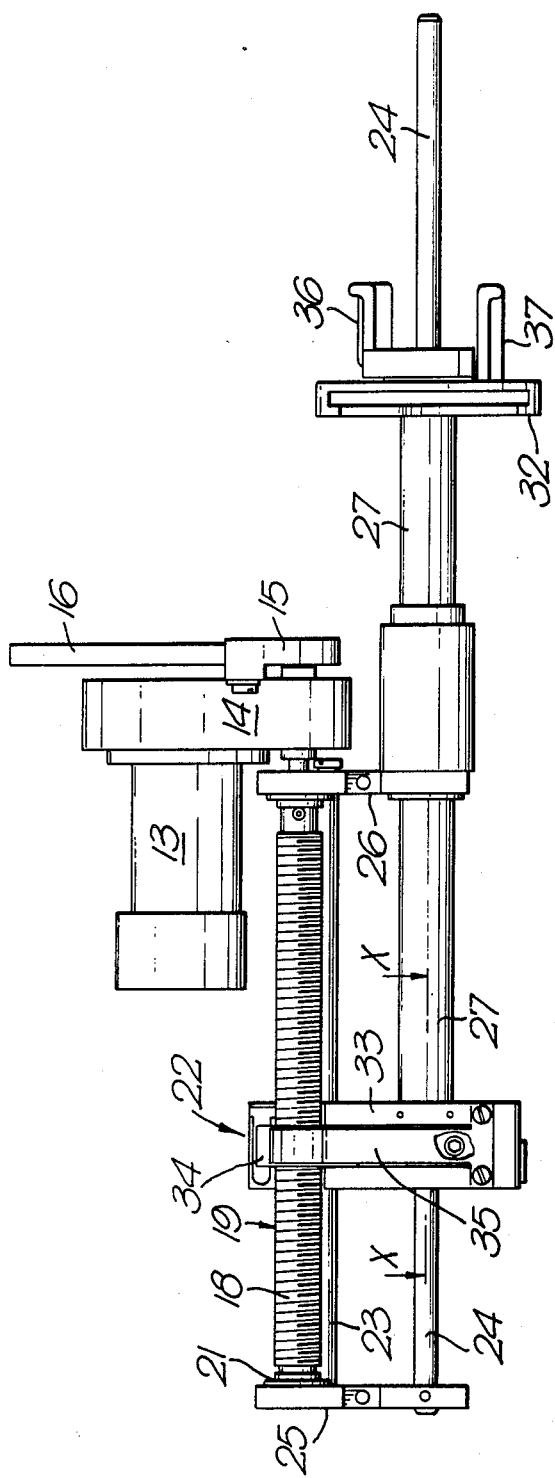
FIG. 5 is a plan view of the major components housed in the lower case assembly.

Referring now to FIGS. 1-4 of the drawings, the syringe pump includes an upper casing part 1 and a lower casing part 2. In the upper casing part 1 there is a control/display panel 3 incorporating touch-sensitive control buttons 4 and a display panel 5. The upper casing part 1 includes an aperture 6 whose function will become apparent in due course. Mounted externally on the main body of upper casing part 1 is a rotary clamp means 7 shown partly cut away in FIG. 1 to reveal a clamp spring 8 and a rotary potentiometer 9 (not shown in FIG. 3). Clamp means 7 includes a flange 10 having a shoulder 11 which is urged by spring 8 in the clockwise direction as viewed from the right, i.e. in a sense tending to clamp a syringe (not shown) between shoulder 11 and casing surface portion 12. A printed circuit board 30 is mounted below display panel 3, as shown in FIG. 4.

Figure 6:
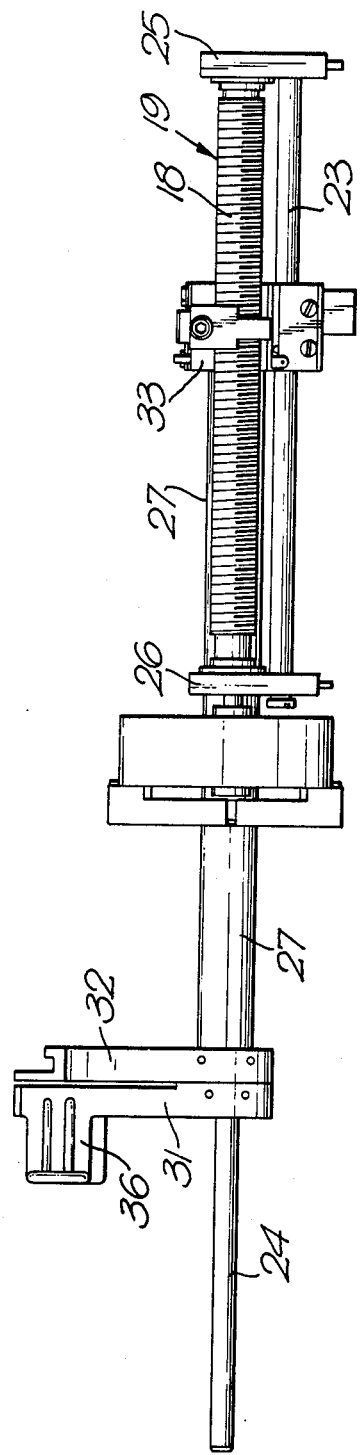
FIG. 6 is a side elevational view of the elements shown in FIG. 5, but seen from behind.

Within the body of the syringe pump there is mounted a motor and transmission assembly which is illustrated in FIGS. 5-8. Motor 13 is housed within a casing which also houses a gear box 14. An arcuate beam 15 supports gear box 14. A flat beam 16 carries a strain gauge 17. Motor 13 is connected through gear box 14 to drive a drive rod 18 which is externally screw-threaded as shown at 19. At that end 20 of drive rod 18 which is remote from gear box 14, the rod is free to rotate in a journal bearing 21. The carriage assembly 22 comprising a first or outer part 33 and a second or inner part 34 is driveably engaged through its part 34 with drive rod 18 and is slidably supported by a first support rod 23 and a second support rod 24. Support rod 23 is fixed between plates 25 and 26 which in turn are rigidly mounted on the lower casing part 2. Support rod 24 is fixed at one end to plate 25 and at its other end it passes beneath the aperture 6 in upper casing 1 and is secured to the lower casing framework.

Drive from motor 13 via gearbox 14 causes shaft 18 to rotate. When the inner part 34 of carriage 22 is engaged on shaft 18, rotation of the shaft causes lateral movement of the carriage which, when the assembly is in use, exerts pressure on the plunger of a syringe mounted in the gap between shoulder 11 and surface 12 (see FIG. 4). In order to disengage carriage 22 from shaft 18, a de-clutch arrangement is provided. This comprises a lever de-clutch 31 carrying a lever 36 which is mounted about rod 24 adjacent to a syringe holder/plunger 32 which also carries a projection 37. Both of parts 31 and 32 extend upwardly through the aperture 6 of upper casing unit 1 when the two casing parts are engaged. Located coaxially about rod 24 is an intermediate tube 28 and an outer tube 27 (see FIG. 8). Outer tube 27 is fixed at one end to holder/plunger 32 and at its other end to the outer part 33 of carriage assembly 22. Intermediate tube 28 is connected at one end to lever declutch 31 and at its other end to the inner part 34 of carriage assembly 22. A leaf-spring 35 is attached to the outer part 33 of carriage assembly 22 and bears against the inner part 34 thereof, as best seen in FIGS. 1 and 7. Spring 35 urges part 34 against screw thread 19 of shaft 18.

In order to de-clutch the carriage 22 from shaft 18, lever part 36 of lever de-clutch 31 is brought to bear against the correspondingly shaped projection 37 which is fixed to plunger 32. This causes intermediate tube 28 to rotate, thereby lifting part 34 upwardly away from shaft 18 against the biassing force of spring 35. When the manual force holding parts 36 and 37 together is released, leaf spring 35 causes the inner part 34 of carriage assembly 22 to re-engage with drive shaft 18.

The inner part 34 of carriage assembly 22 is preferably constructed in the manner shown schematically in FIG. 9. The part is formed of phosphor bronze and comprises elements 40 and 41 which are screwed together as indicated by the bore 42. Element 40 includes a hemispherical recess 43 which is screw-threaded and which cooperates with the screw-thread 19 of shaft 18. The inner assembly unit is carried on rod 24 which passes through the recess 43 in part 41. We have found that the two-part construction illustrated in FIG. 9 gives optimum performance while allowing for constructional tolerances and preventing accidental disengagement of the assembly from drive screw 18.

Carriage 22 supports, on its lower surface, a reader unit 39 which includes a double optical switch arrangement. Unit 39 cooperates with a two-channel linear encoder 38 which is fixed to lower casing part 2. The two light beams of the reader unit 39 are directed at the two channels of the linear encoder 38, the markings of which are such that an absolute position indication is derivable from the output of the unit 39 at any point along linear encoder 38. The printed circuit board 30 includes a microprocessor which responds to input commands from control buttons 4 and processes the output signals generated by rotary potentiometer 9, strain gauge 17 and reader unit 39 to determine, inter alia, (i) the amount of fluid delivered from a syringe held between shoulder 11 and surface part 12; and (ii) the fluid delivery pressure from said syringe. The microprocessor also generates signals which activate display within display panel 5 and monitors the performance of the syringe pump so that, if any predetermined safety parameters are violated, an alarm signal is generated.

When a pre-set delivery rate is keyed into the syringe pump unit, the microprocessor converts this rate into a numerical code which corresponds to a pulse rate which in turn is applied to motor 13. The microprocessor counts the number of "OM" pulses and this enables the position of the syringe to be determined relative to the start position; hence the quantity of infusion liquid delivered can be calculated and displayed.

Preferably, when the unit is completing delivery from a syringe, the microprocessor is arranged to slow down motor 13 so that the last few milliliters of infusion liquid are delivered at a reduced rate which is independent of the pre-set delivery rate. When this condition is reached, the microprocessor can actuate an alarm to warn an operative that the end of the infusion is approaching. This reduced rate delivery towards the end of infusion also avoids problems which can arise at the end of an infusion cycle when air may be injected into a vein or when a vein may tend to close.

What is claimed is:

1. A syringe pump for actuating a syringe having a plunger element which comprises:
   (a) a casing;
   (b) within said casing, a motor;
   (c) an externally screw-threaded drive rod connected at one end thereof to said motor so that, in use, the motor can rotate the drive rod about its axis, the other end of said drive rod being free to rotate in a journal bearing;
   (d) a carriage mounted for sliding movement within said casing and driveably mounted on said drive rod in engagement with the external screw-thread thereof said carriage actuating said plunger element;
   (e) a strain gauge operatively connected to measure the torque reaction between said motor and said carriage when the carriage acts, in use, against the plunger element of the syringe to expel fluid from the syringe;
   (f) means located externally of the main body of the casing for holding the syringe in position on the syringe pump;
   (g) means for sensing the position of said carriage with respect to the ends of said drive rod;
   (h) a microprocessor arranged to receive input signals from said string gauge and said carriage position sensing means and to derive therefrom (when the syringe pump is in use) firstly the fluid delivery rate and secondly the fluid delivery pressure; and
   (i) a control system, acting through said microprocessor, to input operating commands to the syringe pump.

2. A syringe pump as claimed in claim 1, which further comprises: (j) a display system driven by said microprocessor to display a predetermined set of parameters relating to the operating condition of the syringe pump.

3. A syringe pump as claimed in claim 1, wherein said carriage is supported within the casing on one or more fixed rods.

4. A syringe pump as claimed in claim 3, wherein said carriage comprises two parts, one of which parts is supported by said rod(s) in a fixed orientation, and the other of which is movable to a limited extent with respect to the first part.

5. A syringe pump as claimed in claim 4, wherein said second carriage part is able to pivot against the action of a biasing means away from engagement with said drive rod.

6. A syringe pump as claimed in claim 5, wherein a declutch arrangement is provided to control the engagement and disengagement of said second carriage part from the drive rod.

7. A syringe pump as claimed in claim 1, wherein said means for sensing the position of the carriage comprises a reader unit attached to the carriage and positioned so as to read a position code.

8. A syringe pump as claimed in claim 7, wherein said code is carried by a bar coded member.

9. A syringe pump as claimed in claim 8, wherein said bar coded member is a two-channel linear encoder located in the syringe pump casing at a level just beneath said carriage.

10. A syringe pump as claimed in claim 1, wherein the means for supporting the syringe is in the form of rotary clamp means located externally of the main body of the casing.

11. A syringe pump as claimed in claim 10, wherein said rotary clamp means incorporates or co-operates with a position sensing device which in use generates a signal indicative of the position of the rotary clamp means about the body of the syringe.

12. A syringe pump as claimed in claim 11, wherein said position sensing device is a rotary potentiometer.

13. A syringe pump as claimed in claim 1, wherein the casing of the syringe pump comprises an upper part and a lower part.

14. A syringe pump for actuating a syringe having a plunger element which comprises:
   (a) a casing;
   (b) within said casing, a variable speed motor;
   (c) an externally screw-threaded drive rod connected at one end thereof to said motor so that, in use the motor can rotate the drive rod about its axis, the other end of said drive rod being free to rotate in a journal bearing;
   (d) a first support rail extending parallel to said drive rod;
   (e) a second support rod extending parallel to said drive rod and to said first support rail;
   (f) a carriage mounted for sliding movement on said first and second support rails and driveably mounted on said drive rod in engagement with the external screw-thread thereof said carriage actuating said plunger element;
   (g) a strain gauge operatively connected to measure the torque reaction between said motor and said carriage when the carriage acts, in use, against the plunger element of the syringe to expel fluid from the syringe;

(h) rotary clamp means located externally of the main body of the casing and incorporating an analog position sensing device capable in use of generating an output signal indicative of the position of the rotary clamp means about the body of the syringe;
(i) extending parallel to said drive rod and cooperating with said carriage, a two-channel linear encoder;
(j) a reader unit attached to said carriage and arrange to read the channels of said linear encoder;
(k) a microprocessor arranged to receive input signals from said strin gauge, said rotary clamp means and said reader unit and programmed to derive therefrom (when the syringe pump is in use) firstly the fluid delivery rate and secondly the fluid delivery pressure;
(l) a control system, acting through said microprocessor, to input operating commands to the syringe pump; and
(m) a display system driven by said microprocessor to display a predetermined set of parameters relating to the operating condition of the syringe pump.

* * * * *

UNITED STATES PATENT AND TRADEMARK OFFICE
CERTIFICATE OF CORRECTION

PATENT NO. : 4,767,406

DATED : August 30, 1988

INVENTOR(S) : Paul Wadham, Walter H. Cox, and Ching B. Lim

It is certified that error appears in the above-identified patent and that said Letters Patent is hereby corrected as shown below:

Column 5, line 12, "display" should read "displays"

Column 5, line 27, "milliliters" should read "millilitres"

Column 6, line 57, "rod" should read "rail"

Signed and Sealed this

Fourteenth Day of March, 1989

*Attest:*

DONALD J. QUIGG

*Attesting Officer*   *Commissioner of Patents and Trademarks*